US011625834B2

(12) United States Patent
Xu et al.

(10) Patent No.: US 11,625,834 B2
(45) Date of Patent: Apr. 11, 2023

(54) SURGICAL SCENE ASSESSMENT BASED ON COMPUTER VISION

(71) Applicant: Sony Corporation, Tokyo (JP)

(72) Inventors: Wanxin Xu, San Jose, CA (US); Ko-Kai Albert Huang, Cupertino, CA (US)

(73) Assignee: Sony Group Corporation, Tokyo (JP)

( * ) Notice: Subject to any disclaimer, the term of this patent is extended or adjusted under 35 U.S.C. 154(b) by 190 days.

(21) Appl. No.: 16/808,265

(22) Filed: Mar. 3, 2020

(65) Prior Publication Data

US 2021/0142487 A1 May 13, 2021

Related U.S. Application Data

(60) Provisional application No. 62/932,595, filed on Nov. 8, 2019.

(51) Int. Cl.
*G06K 9/00* (2022.01)
*G06T 7/20* (2017.01)
*A61B 34/20* (2016.01)
*G06T 7/70* (2017.01)
*A61B 90/00* (2016.01)
(Continued)

(52) U.S. Cl.
CPC ............... *G06T 7/20* (2013.01); *A61B 34/20* (2016.02); *G06T 7/70* (2017.01); *A61B 5/02042* (2013.01); *A61B 90/361* (2016.02); *A61B 2034/2065* (2016.02); *A61B 2218/008* (2013.01); *A61F 13/44* (2013.01); *G06T 2207/10016* (2013.01); *G06T 2207/20084* (2013.01)

(58) Field of Classification Search
CPC .............................................. A61B 2034/2065
See application file for complete search history.

(56) References Cited

U.S. PATENT DOCUMENTS 8,845,667 B2 * 9/2014 Cruz Hernandez .... A61B 17/28
606/174
10,242,292 B2 3/2019 Zisimopoulos et al.
(Continued)

FOREIGN PATENT DOCUMENTS

JP 2011036372 A 2/2011
JP 2015228955 A 12/2015
(Continued)

OTHER PUBLICATIONS

"Real-Time Segmentation of Non-Rigid Surgical Tools based on Deep Learning and Tracking" https://www.researchgate.net/publication/305770331_Real-Time_Segmentation_of_Non-Rigid_Surgical_Tools_based_on_Deep_Learning_and_Tracking.
(Continued)

*Primary Examiner* — Hadi Akhavannik
(74) *Attorney, Agent, or Firm* — Trellis IP Law Group, PC

(57) ABSTRACT

Implementations generally relate to surgical scene assessment based on computer vision. In some implementations, a method includes receiving a first image frame of a plurality of image frames associated with a surgical scene. The method further includes detecting one or more objects in the first image frame. The method further includes determining one or more positions corresponding to the one or more objects. The method further includes tracking each position of the one or more objects in other image frames of the plurality of image frames.

19 Claims, 9 Drawing Sheets

(51) Int. Cl.
   *A61B 5/02* (2006.01)
   *A61F 13/44* (2006.01)

(56) References Cited

U.S. PATENT DOCUMENTS

| | | | |
|---|---|---|---|
| 2006/0258938 A1* | 11/2006 | Hoffman | A61B 5/06 600/424 |
| 2007/0270685 A1* | 11/2007 | Kang | A61B 34/76 600/424 |
| 2010/0131532 A1 | 5/2010 | Schultz | |
| 2012/0207359 A1 | 8/2012 | Konukoglu | |
| 2013/0113929 A1 | 5/2013 | DeLand | |
| 2014/0018821 A1* | 1/2014 | Yeung | A61B 34/71 606/130 |
| 2014/0031659 A1* | 1/2014 | Zhao | A61B 1/07 600/371 |
| 2014/0094968 A1* | 4/2014 | Taylor | B25J 13/006 700/257 |
| 2015/0003704 A1 | 1/2015 | Nomura et al. | |
| 2015/0170381 A1* | 6/2015 | Liu | G06T 7/74 348/77 |
| 2016/0259888 A1* | 9/2016 | Liu | G16H 70/20 |
| 2017/0289504 A1 | 10/2017 | Fridental | |
| 2018/0221102 A1* | 8/2018 | Wang | A61B 17/29 |
| 2019/0038362 A1* | 2/2019 | Nash | G02B 27/0172 |
| 2019/0104919 A1* | 4/2019 | Shelton, IV | A61B 90/361 |

FOREIGN PATENT DOCUMENTS

| | | | |
|---|---|---|---|
| JP | 2018068863 A | 5/2018 |
| JP | 2018515857 A | 6/2018 |
| JP | 2019505898 A | 2/2019 |
| WO | WO-2017098505 A1 | 6/2017 |

OTHER PUBLICATIONS

Chang Shuo et al: 11 Siamese Feature Pyramid Network for Visual Tracking 11 , 2019 IEEE/CIC International Conference on Communications Workshops in China (ICCC Workshops). IEEE, Aug. 11, 2019 (Aug. 11, 2019), pp. 164168,XP033621181,DOI: 10.1109/ICCCHINAW.2019.8849954[retrieved on Sep. 25, 2019] * 1. Introduction;p. 164 *.

Diana Martins Lavada: Sorting Surgical Tools from a Cluttered Tray—Object Detection and Occlusion Reasoning Imagem, Sep. 28, 2018 (Sep. 28, 2018), XP055670808, Retrieved from the Internet: URL: https://estudogeral.uc.pt/bitstream/10316/86257/1/Tese-Diana VersaoFinal.pdf [retrieved on Feb. 21, 2020]* second point;p. 20 *.

Garcia-Marti Nez Alvaro et al: 11 Automatic detection of surgical gauzes using Computer Vision11, 2015 23rd Mediterranean Conference on Control and Automation (MED), IEEE, Jun. 16, 2015 (Jun. 16, 2015), pp. 747-751, XP033176504, DOI: 10 .1109/MED. 2015. 7158835 [retrieved on Jul. 14, 2015] *abstract*.

Gomariz Alvaro et al: Siamese Networkswith Location Prior for Landmark Tracking in Liver Ultrasound Sequences 11 , 2019 IEEE 16th International Symposium on Biomedical Imaging (ISBI 2019). IEEE, Apr. 8, 2019 (Apr. 8, 2019), pp. 1757-1760, XP033576513, DOI: 10.1109/ISBI.2019.8759382 [retrieved on Jul. 10, 2019] * 4. Conclusion; p. 1760 *.

Leibetseder Andreas et al: 11 Image-Based Smoke Detection in Laparoscopic Videos 11, Sep. 8, 2017 (Sep. 8, 2017), ICIAP: International Conference on Image Analysis and Processing, 17th International Conference, Naples, Italy, Sep. 9-13, 2013. Proceedings; [Lecture Notes in Computer Science; Lect.Notes Computer], Springer, Berlin, Heidelberg, pp. 70-87, XP047435533, ISBN: 978-3-642-17318-9 [retrieved on Sep. 8, 2017] *abstract*.

Yanan Fu et al: 11 Bleeding region detection in WCE images based on color features and neural network11 , Circuits and Systems (MWSCAS). 2011 IEEE 54th International Midwest Symposium on, IEEE, Aug. 7, 2011 (Aug. 7, 2011), pp. 1-4, XP031941470, DOI: 10 .1109/MWSCAS. 2011. 6026527 ISBN: 978-1-61284-856-3 *abstract*.

Zhou Lijun et al: 11 Combined Kalman Filter and Multifeature Fusion Siamese Network for Real-Time Visual Tracking 11 , Sensors, vol. 19, No. 9, May 1, 2019 (May 1, 2019), p. 2201,XP055788894,DOI:10.3390/s19092201 Retrieved from the Internet:URL:https://www.ncbi.nlm.nih.gov/pmc/artic les/PMC6539506/pdf/sensors1902201.pdf>*Section 3;p. 4-p. 7 *.

* cited by examiner

SURGICAL SCENE ASSESSMENT BASED ON COMPUTER VISION

CROSS REFERENCES TO RELATED APPLICATIONS

This application claims the benefit of U.S. Provisional Patent Application Ser. No. 62/932,595, entitled "A Surgical Scene Understanding System with Computer Vision-based Detection and Tracking", filed on Nov. 8, 2019, which is hereby incorporated by reference as if set forth in full in this application for all purposes.

BACKGROUND

Computer-assisted surgery uses computer technology for guiding or performing medical procedures such as procedures involving endoscopy, laparoscopy, etc. During surgery, a surgeon may need to use various tools to perform surgery. A camera and monitor can help a surgeon to perform surgery procedures. However, surgical camera or video sequences are underutilized.

SUMMARY

Implementations generally relate to surgical scene assessment based on computer vision. In some implementations, a system includes one or more processors, and includes logic encoded in one or more non-transitory computer-readable storage media for execution by the one or more processors. When executed, the logic is operable to cause the one or more processors to perform operations including: receiving a first image frame of a plurality of image frames associated with a surgical scene; detecting one or more objects in the first image frame; determining one or more positions corresponding to the one or more objects; and tracking each position of the one or more objects in other image frames of the plurality of image frames.

With further regard to the system, in some implementations, at least one object of the one or more objects is a surgical tool. In some implementations, at least one object of the one or more objects is a gauze. In some implementations, at least one object of the one or more objects is a bleeding region. In some implementations, at least one object of the one or more objects is smoke. In some implementations, the detecting of the one or more objects in the first image frame is performed utilizing a convolutional neural network. In some implementations, the operations are performed in real-time.

In some embodiments, a non-transitory computer-readable storage medium with program instructions thereon is provided. When executed by one or more processors, the instructions are operable to cause the one or more processors to perform operations including: receiving a first image frame of a plurality of image frames associated with a surgical scene; detecting one or more objects in the first image frame; determining one or more positions corresponding to the one or more objects; and tracking each position of the one or more objects in other image frames of the plurality of image frames.

With further regard to the computer-readable storage medium, in some implementations, at least one object of the one or more objects is a surgical tool. In some implementations, at least one object of the one or more objects is a gauze. In some implementations, at least one object of the one or more objects is a bleeding region. In some implementations, at least one object of the one or more objects is smoke. In some implementations, the detecting of the one or more objects in the first image frame is performed utilizing a convolutional neural network. In some implementations, the operations are performed in real-time.

In some implementations, a method includes: receiving a first image frame of a plurality of image frames associated with a surgical scene; detecting one or more objects in the first image frame; determining one or more positions corresponding to the one or more objects; and tracking each position of the one or more objects in other image frames of the plurality of image frames.

With further regard to the method, in some implementations, at least one object of the one or more objects is a surgical tool. In some implementations, at least one object of the one or more objects is a gauze. In some implementations, at least one object of the one or more objects is a bleeding region. In some implementations, at least one object of the one or more objects is smoke. In some implementations, the detecting of the one or more objects in the first image frame is performed utilizing a convolutional neural network.

A further understanding of the nature and the advantages of particular implementations disclosed herein may be realized by reference of the remaining portions of the specification and the attached drawings.

DETAILED DESCRIPTION

Implementations described herein enable and facilitate the assessment of a surgical scene based on computer vision. A system utilizes a deep learning based approach for object detection and tracking. As described in more detail herein, in various embodiments, a system receives a video stream capturing a surgical scene. The video stream includes image frames that contain one or more objects in a surgical scene. For example, objects may include surgical tools, gauzes, bleeding regions, smoke, etc. The system detects the one or more objects across different images frames of the video stream. The system then determines positions corresponding to the detected objects. The system also tracks each position of the objects across the different image frames of the video stream. The detection and tracking provide appearance and trajectory information for tools, gauze, blood and smoke. Further analysis of tool usage patterns, range of movement or time usage may be useful to a surgeon in real-time or post-surgery in operation room.

Figure 1:
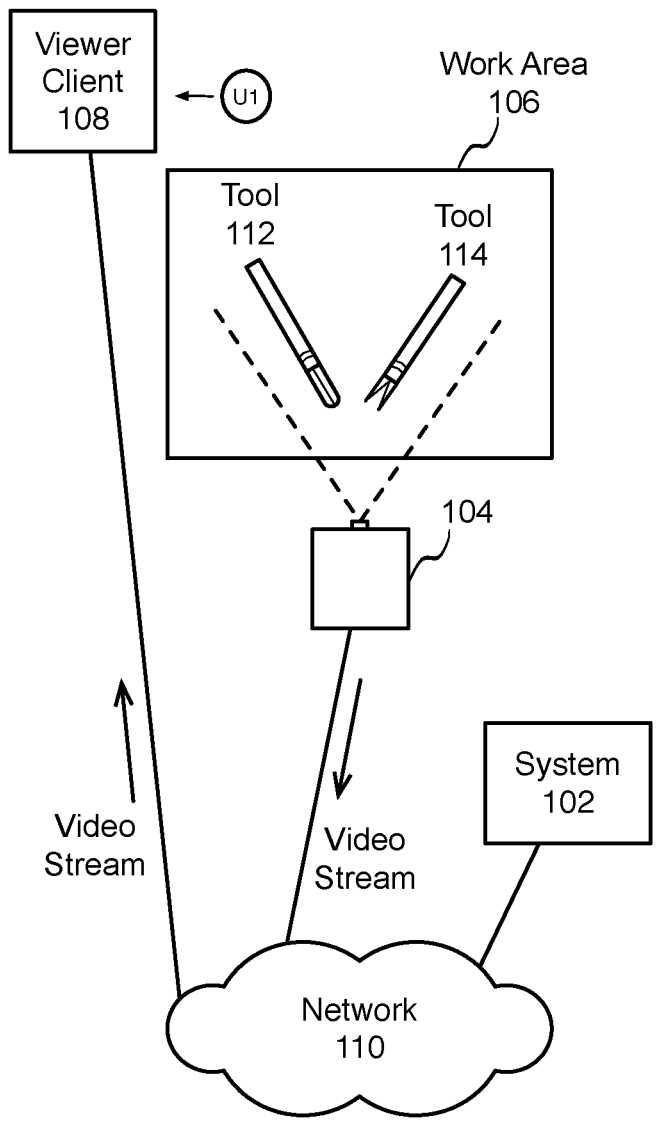
FIG. 1 illustrates a block diagram of an example work environment, which may be used for implementations described herein.

FIG. 1 illustrates a block diagram of an example work environment 100 which may be used for implementations described herein. Shown is a surgical scene analytic system 102, or system 102, which performs various implementations described herein. System 102 controls a camera 104, which captures video of a surgical scene in a work area 106. System 102 causes camera 104 to send a video stream from camera 104 to viewer client 108 via a network 110. As described in more detail herein, system 102 analyzes the characteristics of tools 112 and 114, which are captured by camera 104. Network 110 may be any suitable communication network such as a Wi-Fi network, Bluetooth network, the Internet, etc. In various implementations, work environment 100 may not have all of the components shown and/or may have other elements including other types of components instead of, or in addition to, those shown herein.

As described in more detail herein, with only a camera and no other sensing or detection devices in an operating room, system 102 automatically analyzes a surgical scene without human intervention using computer vision techniques. System 102 may detect and track elements or objects in the surgical scene. Such objects may include, for example, surgical tools, gauzes, bleeding regions, smoke, etc. While various example embodiments are described in the context of surgical tools, gauzes, bleeding regions, and smoke, these embodiments may apply to other types of objects that may appear in a surgical scene and that may be captured by the camera.

In various embodiments, system 102 includes an end-to-end supervised deep architecture for detecting and tracking objects, learning visual features, and enforcing constraints to the detection and tracking pipeline. In various embodiments, system 102 also includes a convolutional neural network based appearance descriptor. In some embodiments, the appearance descriptor may be trained using an architecture such as a Siamese architecture for feature representation and data association of image patches.

Figure 2:
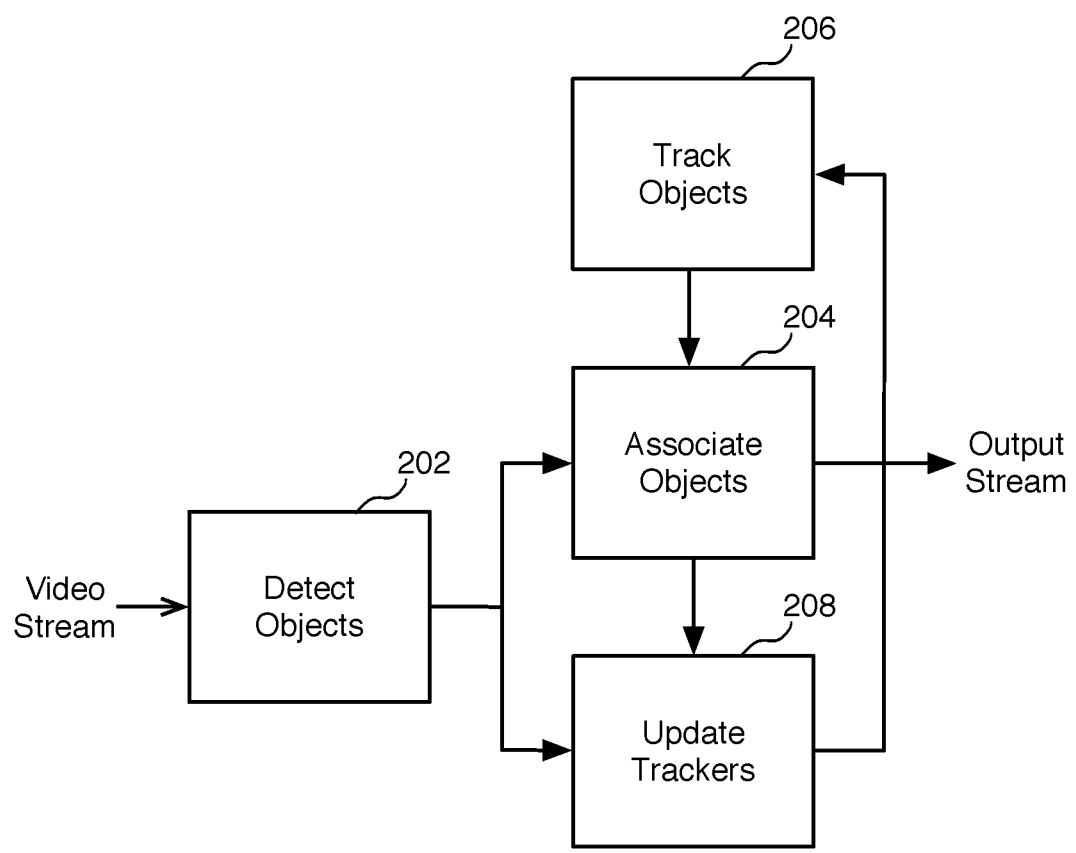
FIG. 2 illustrates an example flow diagram for analyzing a surgical scene, according to some implementations.

FIG. 2 illustrates an example flow diagram for analyzing a surgical scene, according to some implementations. In various embodiments, the flow diagram provides a detection and tracking framework. As shown, at block 202, a system such as system 102 of FIG. 1 detects objects in a received video stream. In various embodiments, the system detects objects in each image frame of a series of images frames of the video stream. For example, system 102 may detect surgical tools, gauzes, bleeding regions, smoke, etc., in an image frame captured by camera 104. The particular types of objects may vary, depending on the particular implementation. In various embodiments, the system classifies the one or more objects into one or more classifications.

In various implementations, the system utilizes a deep learning network to classify the objects into the various object classifications. In some implementations, the system uses a classifier that is trained with known features learned by the deep learning network. The system uses the known features to determine and identify objects based on the features that the system recognizes in the image frame. The system compares the features to known features of objects, and then matches the one or more features to the known features. In various implementations, the system stores information on the known features in a suitable storage location. Any new information may be used to help to identify features of newly detected objects and to help classify those objects. The system then classifies the one or more objects into the one or more tool classifications based on the matching.

At block 204, the system associates each object with a tracker. In various embodiments, the system generates a tracker for each object. In various embodiments, a tracker may be a software algorithm that the system executes to predict and update positions of objects in a scene captured in a video. The system then associates each tracker with a respective object. For example, the system may generate a first tracker for a first object and a second tracker for a second object, which results in one tracker per object. In any given subsequent image frame, if the system detects a new or third object, the system then generates a new or third tracker. As described in more detail herein, the system tracks each object from image frame to image frame using the same associated tracker for each object. As such, the system iteratively detects and tracks objects in the video stream (e.g., frame to frame, etc.).

At block 206, the system tracks the detected objects. As indicated above, the system associates a new tracker for each new object that the system detects in across the image frames of the video stream. In various embodiments, the system utilizes a tracker to track a given object from one frame to another frame using any suitable tracking techniques (e.g., distance metric, appearance descriptor, etc.).

In various embodiments, the system predicts and updates the position of each object in the image frames of the video stream (e.g., using a Kalman filter, etc.). The system may utilize a convolutional neural network with a feature pyramid network (e.g., Darknet, etc.) to detect objects.

In various embodiments, the system tracks each object, including maintaining recognition of each object over time and over different image frames in which each object appears. In various embodiments, the system determines the current position of a given object and also predicts future positions of the given object based on current position (e.g., using a Kalman filter, extended Kalman filter, particle filter, etc.). In various embodiments, the system may generate and associate various information with each object utilizing any suitable techniques, including, for example, a convolutional neural network (e.g., a Siamese network) for appearance matching, and a distance metric (e.g., Euclidean distance or cosine distance) and/or an overlap metric (e.g., intersection over union or IoU) for location matching, etc.

At block 208, the system updates each tracker. In various embodiments, the system updates the location of each object for each subsequent image frame detected in the video stream. As such, the system may track the movement of any given object in the video stream.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

As described in more detail below, in various embodiments, the system extracts useful information from the video stream, such as types of tools, tool states, bleeding regions, gauzes, smoke levels, etc., automatically from the surgery cameras or videos. Further example implementations directed to these steps are described in more detail herein.

Figure 3:
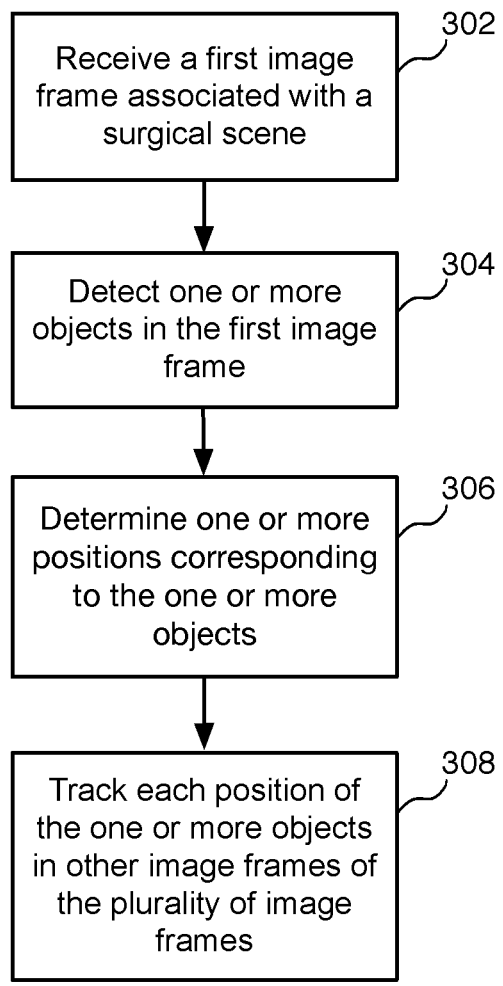
FIG. 3 illustrates an example flow diagram for assessing a surgical scene based on computer vision, according to some implementations.

FIG. 3 illustrates an example flow diagram for assessing a surgical scene based on computer vision, according to some implementations. Referring to both FIGS. 1 and 2, a method is initiated at block 302, where a system such as system 102 receives a first image frame associated with a surgical scene. The first image frame is one image frame of a series or sequence of image frames in a video stream.

At block 304, the system detects one or more objects in the first image frame. In various implementations, the system may use object recognition techniques to detect objects in the received image frame. As indicated above, the system may use a convolutional neural network to identify and/or recognize objects of interest. In some embodiments, the system may use a feature pyramid network, e.g. Darknet, etc.

At block 306, the system determines one or more positions corresponding to the one or more objects. The system may utilize any suitable techniques for determining the position of each object.

At block 308, the system tracks each position of the one or more objects in other image frames of the plurality of image frames.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

In various embodiments, the system uses computer vision and machine learning to visually recognize various different types of objects such as tools, gauzes, bleeding regions, smoke, etc. for real-time robust analysis of highly variable surgical scenes. As indicated above, in various embodiments, the system may extract useful information from the video stream, such as types of tools, tool states, bleeding regions, gauzes, smoke levels, etc., automatically from the surgery cameras or videos.

Figure 4:
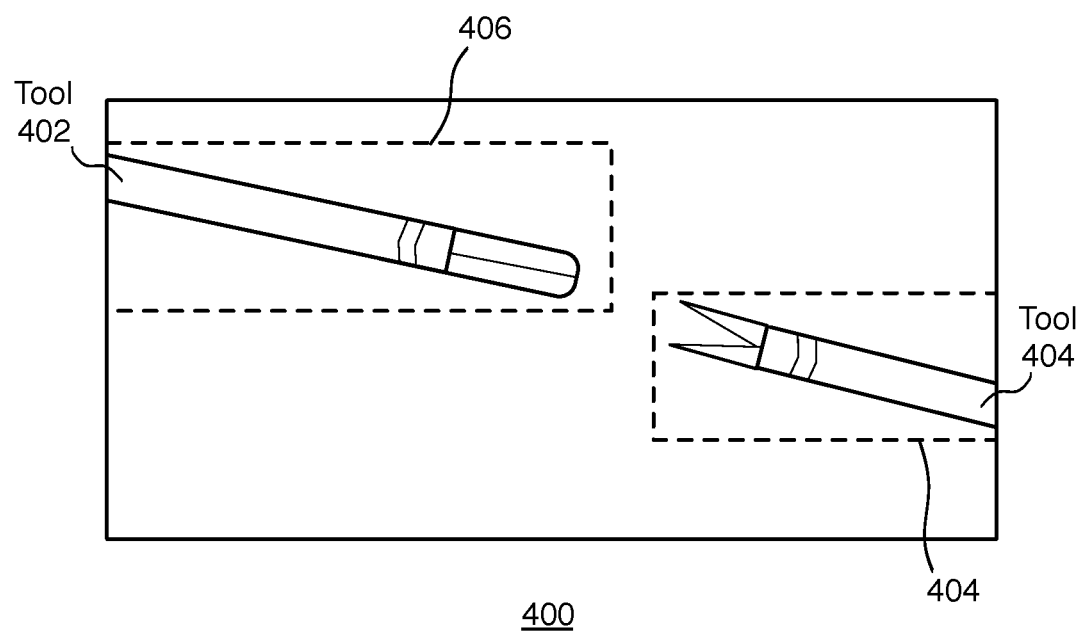
FIG. 4 illustrates example screen shot showing two tools and two corresponding bounding boxes, according to some implementations.

FIG. 4 illustrates example screen shot 400 showing two tools 402 and 404 and two corresponding bounding boxes 406 and 408, according to some implementations. In various embodiments, at least one object of the one or more objects is a surgical tool. In this example, there are two surgical tools. In various embodiments, the system detects the state of each tool in the image. For example, the system may determine if a tool is open or closed. For example, the system may detect a scissor tool and determine the tool state of the scissor tool being open or closed. In some embodiments, the may also determine the degree in which the tool is open or closed. In various embodiments, the system classifies each tool or object to determine the type of tool or object. This may be helpful in improving surgical workflows, training, etc. As shown in the following example embodiments, while some objects are described in the context of surgical tools, the system may detect other types of objects.

In various implementations, the one or more tool classifications indicate the types of tools, including the tool functions. Example tools may include cutting or dissecting instruments such as scalpels, scissors, saws, etc. Tools may include bipolar forceps and irrigators. Tools may include grasping or holding instruments such as smooth and toothed forceps, towel clamps, vascular clamps, organ holders, etc. Tools may include hemostatic instruments such as clamps, hemostatic forceps, atraumatic hemostatic forceps, etc. Tools may include retractor instruments such as C-shaped laminar hooks, blunt-toothed hooks, sharp-toothed hooks, grooved probes, tamp forceps, etc. Tools may include tissue unifying instruments and materials such as needle holders, surgical needles, staplers, clips, adhesive tapes, etc. The particular tools detected may vary, and will depend on the particular implementation. While implementations are described herein in the context of surgical tools, these implementations and others may also apply to other tools (e.g., non-surgical tools such as gauzes, etc.).

In various embodiments, the system generates one or more bounding boxes (e.g., bounding boxes 406 and 408) and displays the bounding boxes in a display screen as a visual indicator for any one or more objects of interest (e.g., surgical tools, gauzes, bleeding regions, smoke, etc. As indicated herein, the particular type of objects may vary, and will depend on the particular implementation.

While example bounding boxes are shown as squares. The actual shape of the visual indicators may be any shape. For example, in some implementations, the bounding box or visual indicator may follow the general shape of a given object. In various implementations, the system may superimpose bounding boxes and any associated labels in real-time over the video frames for the user to view. This helps the user to know which objects are being viewed on the display. In some implementations, the system may enable the user to turn the visual indicators off.

Figure 5:
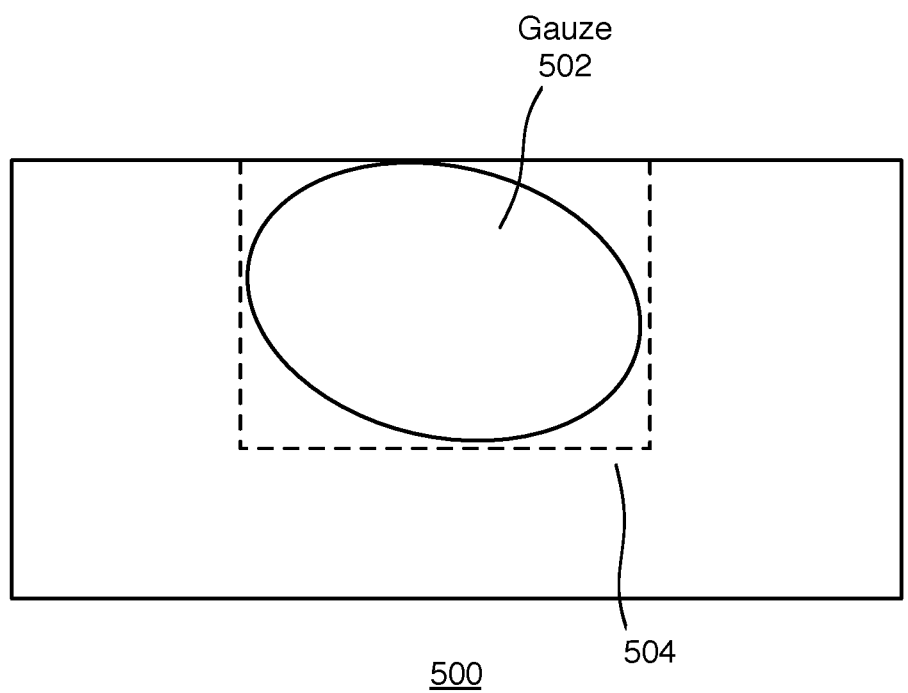
FIG. 5 illustrates example screen shot showing a gauze and a corresponding bounding box, according to some implementations.

FIG. 5 illustrates example screen shot 500 showing a gauze 502 and a corresponding bounding box 504, according to some implementations. In various embodiments, at least one object of the one or more objects is a gauze. This may be helpful in improving the ability of the system in tracking, retrieving, and counting gauzes used in a surgery procedure.

Figure 6:
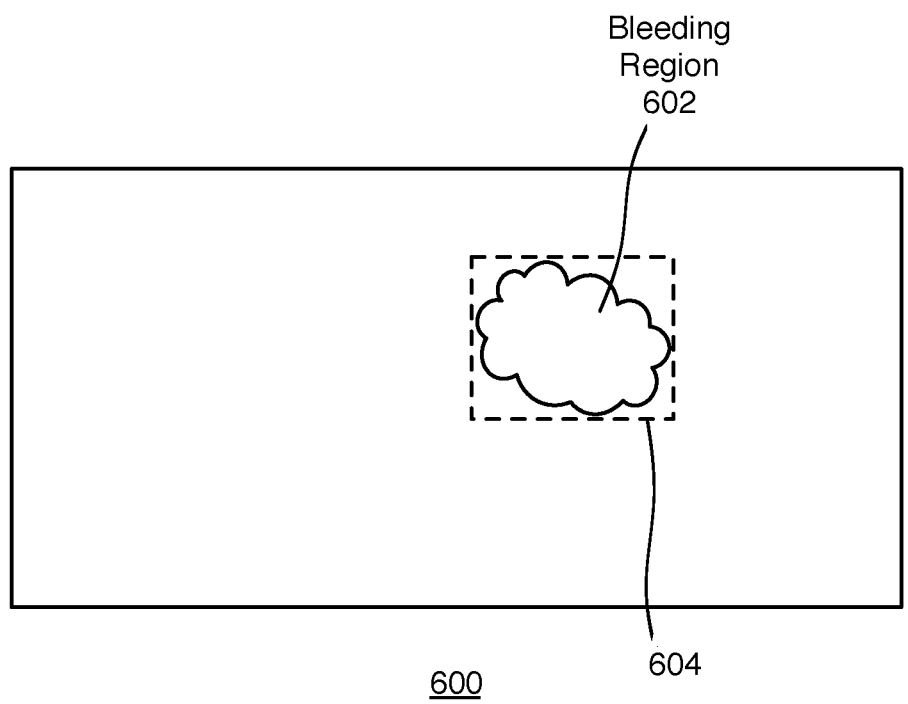
FIG. 6 illustrates example screen shot showing a bleeding region and a corresponding bounding box, according to some implementations.

FIG. 6 illustrates example screen shot 600 showing a bleeding region 602 and a corresponding bounding box 604, according to some implementations. In various embodiments, at least one object of the one or more objects is a bleeding region. This may be helpful in detecting bleeding that a surgeon might not be able to see. For example, the system may visually indicate (e.g., via visual annotations) the bleeding region, direction of blood flow, etc. In various embodiments, the system may also determine bleeding motion estimations in real-time and/or post-process. For example, the system may estimate the direction of detected blood flow, and generate an alert or warning of a bleeding situation.

Figure 7:
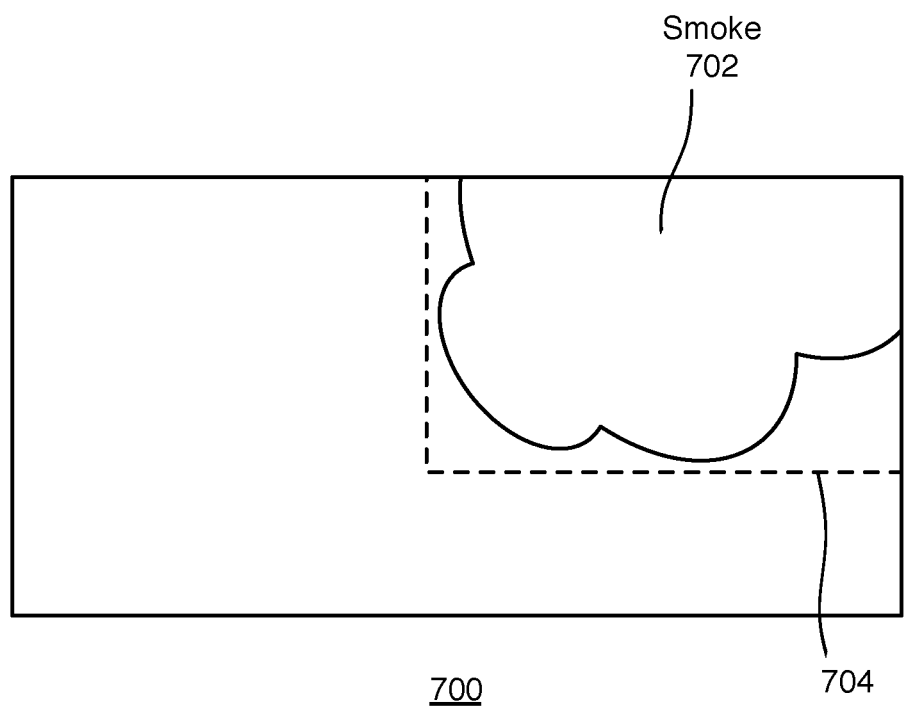
FIG. 7 illustrates example screen shot showing smoke and a corresponding bounding box, according to some implementations.

FIG. 7 illustrates example screen shot 700 showing smoke 702 and a corresponding bounding box 704, according to some implementations. In various embodiments, at least one object of the one or more objects is smoke. This may be helpful in alerting a surgeon to the presence of smoke in the environment but also helpful when using tools to remove smoke in a smoke evacuation procedure. In various embodiments, the system may also determine the amount of smoke (smokiness) in the surgical scene. For example, the system may estimate a level (e.g., 0 . . . 1, etc.) of detected smoke, which may be used in controlling a smoke evacuator.

As indicated above, in various embodiments, the detecting of the one or more objects in the first image frame is performed utilizing a convolutional neural network. In various embodiments, the system performs the operations of blocks 302 through 308 in real-time, enabling the system to perform embodiments described with high accuracy and robustness under highly complex surgical scenes. The system may also perform some post-process operations (e.g., further analysis objects offline at a later time.

The following are additional real-time applications including some additional post-processing operations that may be used as desired. In some implementations, the system may enable and monitor smart (e.g., robotic) surgical navigation to reduce assistants needed during a surgery. In some implementations, the system may monitor and predict surgery progresses for hospital operating room efficiency. In some implementations, the system may provide objective feedback to surgical techniques for surgery procedure education and improvement. In some implementations, the system may analyze the skill and quality of a surgery process. In some implementations, the system may annotate videos in these example applications for fast content management (e.g., search, retrieval, review & editing, etc.).

In various embodiments, the system may handle any variability in the appearance of a given object as the system detects the object in different image frames. For example, the system may detect and classify surgical tools of the same type even if such tools may vary among different tool manufacturers. In various embodiments, the system may handle various surgery dynamics including motion blur, occlusion of other tools and tissues, variations in viewpoints, etc. which increase complexity for tracking, etc. In various embodiments, the system may handle textural ambiguity. For example, the system may detect any shape deformation, dynamic textures, and variable intensities.

Figure 8:
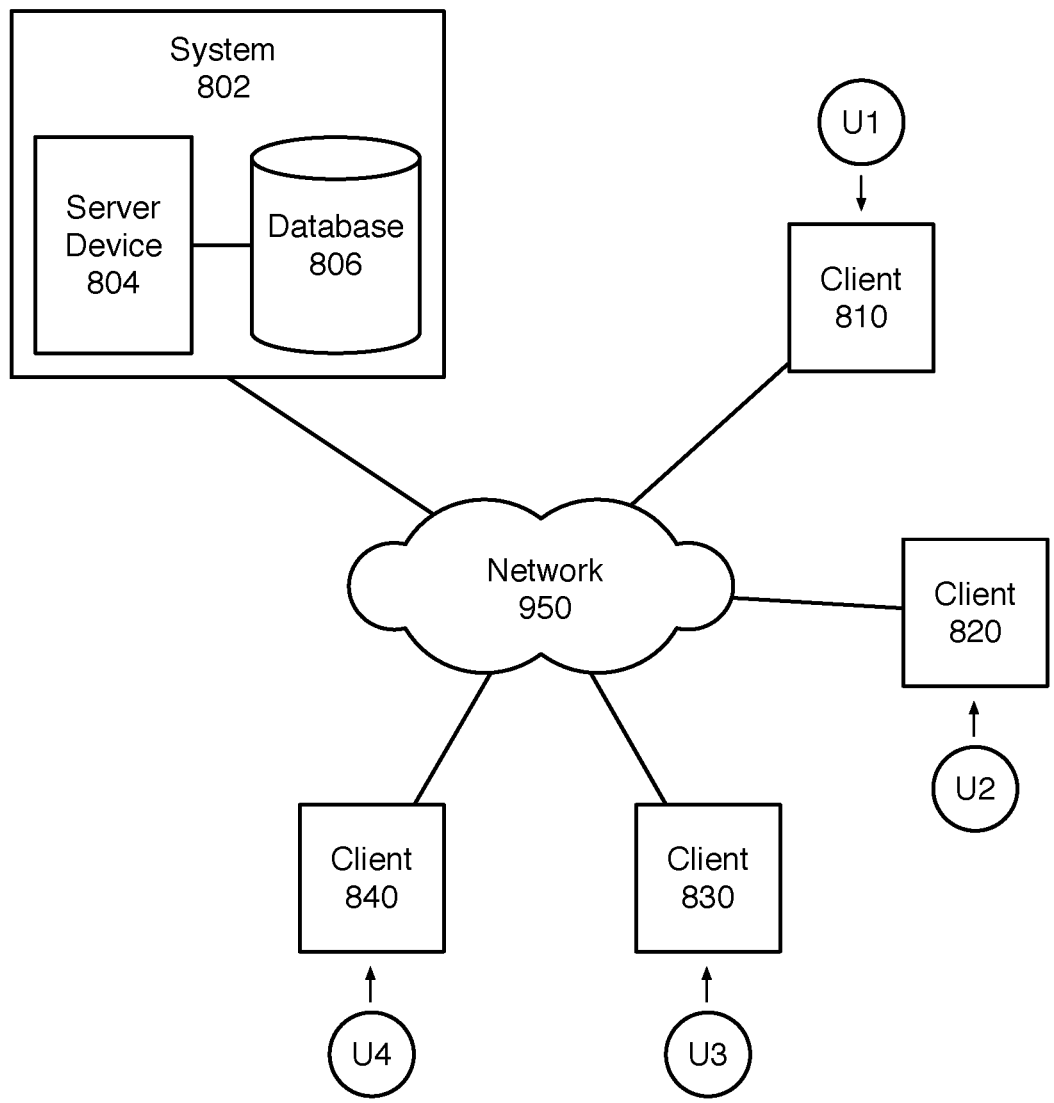
FIG. 8 illustrates a block diagram of an example network environment, which may be used for some implementations described herein.

FIG. 8 illustrates a block diagram of an example network environment 800, which may be used for some implementations described herein. In some implementations, network environment 800 includes a system 802, which includes a server device 804 and a network database 806. For example, system 802 may be used to implement system 102 of FIG. 1, as well as to perform embodiments described herein. Network environment 800 also includes client devices 810, 820, 830, and 840, which may communicate with each other directly or via system 802. Network environment 800 also includes a network 850.

For ease of illustration, FIG. 8 shows one block for each of system 802, server device 804, and network database 806, and shows four blocks for client devices 810, 820, 930, and 840. While some implementations are described in the context of one client device being used to view a video of a surgery procedure (e.g., one surgeon viewing the video), these implementations and others may apply to multiple client devices. For example, there may be other physicians, and/or other clinicians, and/or students viewing the video.

Blocks 802, 804, and 806 may represent multiple systems, server devices, and network databases. Also, there may be any number of client devices. In other implementations, network environment 800 may not have all of the components shown and/or may have other elements including other types of elements instead of, or in addition to, those shown herein. In various implementations, users U1, U2, U3, and U4 may interact with each other or with system 802 using respective client devices 810, 820, 830, and 840.

In the various implementations described herein, a processor of system 802 and/or a processor of any client device 810, 820, 830, and 840 causes the elements described herein (e.g., information, etc.) to be displayed in a user interface on one or more display screens.

Implementations may apply to any network system and/or may apply locally for an individual user. For example, implementations described herein may be implemented by system 802 and/or any client device 810, 820, 830, and 840. System 802 may perform the implementations described herein on a stand-alone computer, tablet computer, smartphone, etc. System 802 and/or any of client devices 810, 820, 830, and 840 may perform implementations described herein individually or in combination with other devices.

Figure 9:
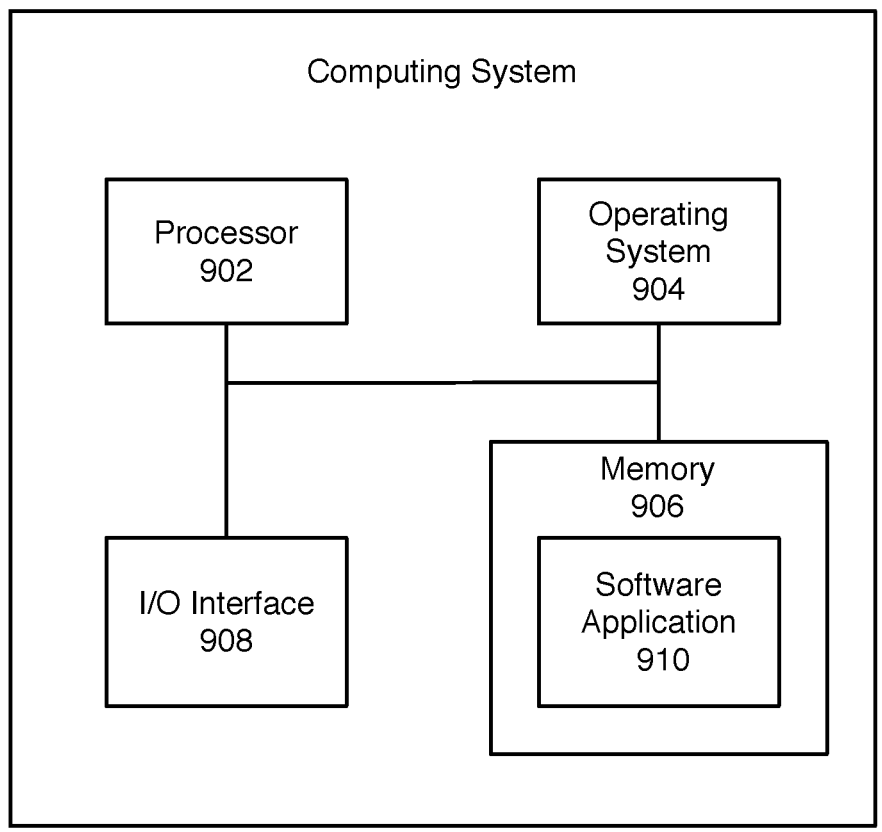
FIG. 9 illustrates a block diagram of an example computing system, which may be used for some implementations described herein.

FIG. 9 illustrates a block diagram of an example computing system 900, which may be used for some implementations described herein. For example, computing system 900 may be used to implement system 102 of FIG. 1 and/or system 802 of FIG. 8, as well as to perform implementations described herein. In some implementations, computing system 900 may include a processor 902, an operating system 904, a memory 906, and an input/output (I/O) interface 908. In various implementations, processor 902 may be used to implement various functions and features described herein, as well as to perform the method implementations described herein. While processor 902 is described as performing implementations described herein, any suitable component or combination of components of computing system 900 or any suitable processor or processors associated with computing system 900 or any suitable system may perform the steps described. Implementations described herein may be carried out on a user device, on a server, or a combination of both.

Computing system 900 also includes a software application 910, which may be stored on memory 906 or on any other suitable storage location or computer-readable medium. Software application 910 provides instructions that enable processor 902 to perform the implementations described herein and other functions. Software application may also include an engine such as a network engine for performing various functions associated with one or more networks and network communications. The components of computing system 900 may be implemented by one or more processors or any combination of hardware devices, as well as any combination of hardware, software, firmware, etc.

For ease of illustration, FIG. 9 shows one block for each of processor 902, operating system 904, memory 906, I/O interface 908, and software application 910. These blocks 902, 904, 906, 908, and 910 may represent multiple processors, operating systems, memories, I/O interfaces, and software applications. In various implementations, computing system 800 may not have all of the components shown and/or may have other elements including other types of components instead of, or in addition to, those shown herein.

Although the description has been described with respect to particular embodiments thereof, these particular embodiments are merely illustrative, and not restrictive. Concepts illustrated in the examples may be applied to other examples and implementations.

In various implementations, software is encoded in one or more non-transitory computer-readable media for execution by one or more processors. The software when executed by one or more processors is operable to perform the implementations described herein and other functions.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a non-transitory computer-readable storage medium (also referred to as a machine-readable storage medium) for use by or in connection with the instruction execution system, apparatus, or device. Particular embodiments can be implemented in the form of control logic in software or hardware or a combination of both. The control logic when executed by one or more processors is operable to perform the implementations described herein and other functions. For example, a tangible medium such as a hardware storage device can be used to store the control logic, which can include executable instructions.

Particular embodiments may be implemented by using a programmable general purpose digital computer, and/or by using application specific integrated circuits, programmable logic devices, field programmable gate arrays, optical, chemical, biological, quantum or nanoengineered systems, components and mechanisms. In general, the functions of particular embodiments can be achieved by any means as is known in the art. Distributed, networked systems, components, and/or circuits can be used. Communication, or transfer, of data may be wired, wireless, or by any other means.

A "processor" may include any suitable hardware and/or software system, mechanism, or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems. A computer may be any processor in communication with a memory. The memory may be any suitable data storage, memory and/or non-transitory computer-readable storage medium, including electronic storage devices such as random-access memory (RAM), read-only memory (ROM), magnetic storage device (hard disk drive or the like), flash, optical storage device (CD, DVD or the like), magnetic or optical disk, or other tangible media suitable for storing instructions (e.g., program or software instructions) for execution by the processor. For example, a tangible medium such as a hardware storage device can be used to store the control logic, which can include executable instructions. The instructions can also be contained in, and provided as, an electronic signal, for example in the form of software as a service (SaaS) delivered from a server (e.g., a distributed system and/or a cloud computing system).

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

What is claimed is:

1. A system comprising:
   one or more processors; and
   logic encoded in one or more non-transitory computer-readable storage media for execution by the one or more processors and when executed operable to cause the one or more processors to perform operations comprising:
   receiving a first image frame of a plurality of image frames associated with a surgical scene;
   detecting one or more objects in the first image frame;
   determining that at least one object of the one or more objects is a scissor tool;
   determining one or more positions corresponding to the one or more objects;
   determining a state of the scissor tool;
   determining a degree in which the scissor tool is open or closed;
   tracking each position of the one or more objects in other image frames of the plurality of image frames; and
   predicting future positions of the one or more objects based on current positions tracked.

2. The system of claim 1, wherein at least one object of the one or more objects is a surgical tool.

3. The system of claim 1, wherein at least one object of the one or more objects is a gauze.

4. The system of claim 1, wherein at least one object of the one or more objects is smoke, and wherein the logic when executed is further operable to cause the one or more processors to perform operations comprising:
   estimating a level of detected smoke; and
   controlling a smoke evacuator based on the level of detected smoke.

5. The system of claim 1, wherein the detecting of the one or more objects in the first image frame is performed utilizing a convolutional neural network.

6. The system of claim 1, wherein the operations are performed in real-time.

7. A non-transitory computer-readable storage medium with program instructions stored thereon, the program instructions when executed by one or more processors are operable to cause the one or more processors to perform operations comprising:
   receiving a first image frame of a plurality of image frames associated with a surgical scene;
   detecting one or more objects in the first image frame;
   determining that at least one object of the one or more objects is a scissor tool;
   determining one or more positions corresponding to the one or more objects;
   determining a state of the scissor tool;
   determining a degree in which the scissor tool is open or closed;
   tracking each position of the one or more objects in other image frames of the plurality of image frames; and
   predicting future positions of the one or more objects based on current positions tracked.

8. The computer-readable storage medium of claim 7, wherein at least one object of the one or more objects is a surgical tool.

9. The computer-readable storage medium of claim 7, wherein at least one object of the one or more objects is a gauze.

10. The computer-readable storage medium of claim 7, wherein at least one object of the one or more objects is a bleeding region.

11. The computer-readable storage medium of claim 7, wherein at least one object of the one or more objects is smoke.

12. The computer-readable storage medium of claim 7, wherein the detecting of the one or more objects in the first image frame is performed utilizing a convolutional neural network.

13. The computer-readable storage medium of claim 7, wherein the operations are performed in real-time.

14. A computer-implemented method comprising:
 receiving a first image frame of a plurality of image frames associated with a surgical scene;
 detecting one or more objects in the first image frame;
 determining that at least one object of the one or more objects is a scissor tool;
 determining one or more positions corresponding to the one or more objects;
 determining a state of the scissor tool;
 determining a degree in which the scissor tool is open or closed;
 tracking each position of the one or more objects in other image frames of the plurality of image frames; and
 predicting future positions of the one or more objects based on current positions tracked.

15. The method of claim 14, wherein at least one object of the one or more objects is a surgical tool.

16. The method of claim 14, wherein at least one object of the one or more objects is a gauze.

17. The method of claim 14, wherein at least one object of the one or more objects is a bleeding region.

18. The method of claim 14, wherein at least one object of the one or more objects is smoke.

19. The method of claim 14, wherein the detecting of the one or more objects in the first image frame is performed utilizing a convolutional neural network.

\* \* \* \* \*